United States Patent [19]

Mizutani et al.

[11] 4,008,268

[45] Feb. 15, 1977

[54] PROCESS FOR ISOMERIZATION OF A CYCLOPROPANECARBOXYLIC ACID

[75] Inventors: Toshio Mizutani, Toyonaka; Nobushige Itaya, Nishinomiya; Toshiko Nishijima, Yokohama; Osamu Magara, Osaka, all of Japan

[73] Assignee: Sumitomo Chemical Company, Limited, Osaka, Japan

[22] Filed: June 10, 1975

[21] Appl. No.: 585,592

[30] Foreign Application Priority Data

June 15, 1974 Japan ............................. 49-68282

[52] U.S. Cl. .......................................... 260/514 H
[51] Int. Cl.[2] ...................................... C07C 61/18
[58] Field of Search ............................... 260/514 H

[56] References Cited

UNITED STATES PATENTS

| | | | |
|---|---|---|---|
| 2,815,362 | 12/1957 | Harper | 260/514 H |
| 3,046,299 | 7/1962 | Julia | 260/514 H |
| 3,538,143 | 11/1970 | Matsui | 260/514 H |
| 3,794,680 | 2/1974 | Matsui | 260/514 H |
| 3,906,026 | 9/1975 | Nagase | 260/514 H |

*Primary Examiner*—Lorraine A. Weinberger
*Assistant Examiner*—Michael Shippen
*Attorney, Agent, or Firm*—Stevens, Davis, Miller & Mosher

[57] ABSTRACT

A process for isomerizing 2-($\beta,\beta$-dichlorovinyl)-3,3-dimethylcyclopropanecarboxylic acid represented by the formula,

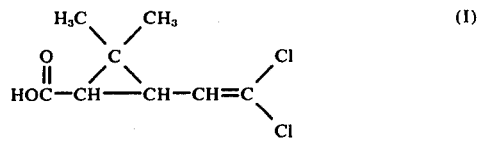

which comprises heating the acid of the formula (I) in the presence of the anhydride of the acid or a reagent producing the acid anhydride in the reaction system.

The ester resulting from 2-($\beta,\beta$-dichlorovinyl)-3,3-dimethylcyclopropanecarboxylic acid and, for example, 3-phenoxybenzyl alcohol is a compound which has a very wide range of insecticidal spectrum and has a very high controlling effect as a low-toxicity insecticide not only for domestic use and public health but also against insects injurious to agriculture or forestry, and in the case of the 3-phenoxybenzyl ester or 5-benzyl-3-furylmethyl ester of the 2-($\beta,\beta$-dichlorovinyl)-3,3-dimethylcyclopropanecarboxylic acid, the trans-isomer is lower than the cis-isomer in toxicity to warm-blooded animals.

6 Claims, No Drawings

PROCESS FOR ISOMERIZATION OF A CYCLOPROPANECARBOXYLIC ACID

The present invention relates to an isomerization process of a cyclopropanecarboxylic acid, and more particularly it relates to a novel isomerization process of a cyclopropanecarboxylic acid represented by the formula,

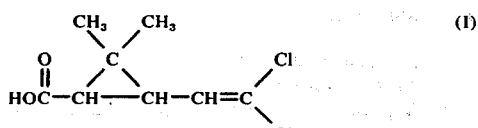

comprising heating a mixture of 2-($\beta,\beta$-dichlorovinyl)-3,3dimethylcyclopropanecarboxylic acid and the anhydride thereof.

2-($\beta,\beta$-Dichlorovinyl)-3,3-dimethylcyclopropanecarboxylic acid (herinafter referred to as dichloro-acid) which is used in the present invention is prepared by the method disclosed in J. Farkas et al.: Chem. listy 52, 688–794 (1958). The ester resulting from the dichloro-acid and, for example, 3-phenoxybenzyl alcohol is a compound which has a very wide range of insecticidal spectrum and has a very high controlling effect as a low-toxicity insecticide not only for domestic use and public health but also against insects injurious to agriculture or forestry. The ester exists in the form of cis- and trans-isomers owing to the three-membered ring of the dichloro-acid. In the case of the 3-phenoxybenzyl ester or 5-benzyl-3-furylmethyl ester of the dichloro-acid, the trans-isomer is lower than the cis-isomer in toxicity to warm-blooded animals.

Therefore, a development of a method has been desired to attain the modification of the cis to trans ratio of dichloro-acid thereby increasing the trans-isomer content, and more preferably to further isolate the trans-isomer alone from the modified dichloro-acid.

In the case of chrysanthemic acid [2-($\beta$-methylpropenyl)-3,3-dimethylcyclopropanecarboxylic acid], such a method is already well known, in which an acid chloride of the acid is subjected to isomerization by heating to produce trans-isomer-rich chrysanthemic acid (in the form of acid chloride). The acid chloride of the dichloro-acid also undergoes isomerization by heating under the same condition to produce trans-isomer-rich dichloro-acid chloride.

In such a heat-isomerization, method however, it is diffucult to isolate the trans-isomer directly from the trans-isomer-rich dichloro-acid chloride thus obtained, that is, for example, the trans-isomer can not easily be isolated by distillation. In order to obtain dichloro-acid ester using quarternary salts of 3-phenoxybenzyl bromide as shown below, a more desirable method is one that enables the isomerization of the dichloro-acid itself or derivatives very close thereto. 3-Phenoxybenzyl ester of the dichloro-acid can easily be obtained by reacting the sodium salt of the dichloro-acid with 3-phenoxybenzyl triethylammonium bromide which can be prepared at a low cost and in a high purity. Therefore, a preferred isomerization process of the dichloro-acid is one where the objective compound after isomerization can be isolated in such a form that can be used directly for the said esterification, for example, in the form of the acid itself or derivatives very close thereto.

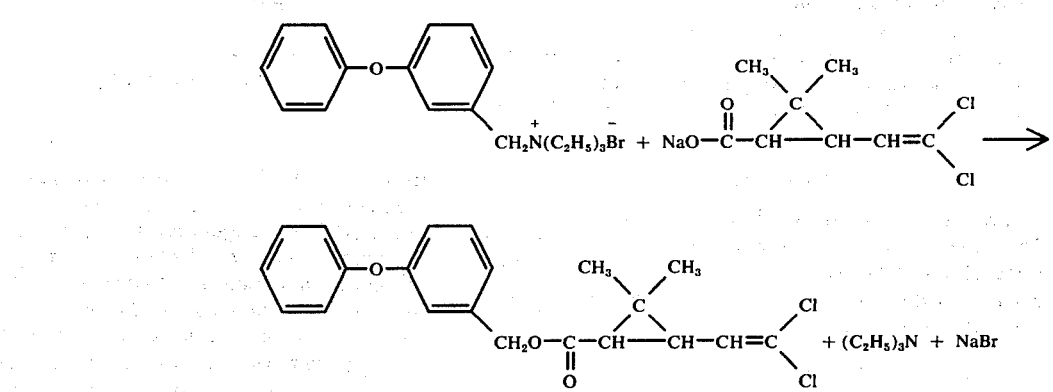

The present inventors have studied isomerization of the dichloro-acid and its derivatives, and found that the dichloro-acid alone hardly undergoes isomerization by heating but the isomerization can be achieved by adding to the acid its acid anhydride. The isomerization occurs even when the dichloro-acid anhydride alone is heated, but it is more preferred to carry out the isomerization in a system containing both the dichoro-acid and dichloro-acid anhydride, because the said esterification is to be carried out, as mentioned above, using the carboxylic acid itself or derivatives very close thereto. The system can provide a rate of isomerization which is industrially useful by controlling the amount of the acid anhydride to be added to the system. Furthermore, simultaneous addition of a small amount of Lewis acid such as p-toluenesulfonic acid or sulfuric acid can further promote the rate of heat-isomerization without an increase of the amount of acid anhydride, and thus can provide an isomerization condition more suitable for the above-metioned object.

Furthermore, it is also possible to add to the system a suitable amount of a reagent which forms the dichloro-acid anhydride in the system, in place of adding the dichloro-acid anhydride itself. The reagent used for this purpose includes acetic anhydride or thionyl chloride.

The objective trans-dichloro-acid can be separated as crystals from the heat-isomerized dichloro-acid thus obtained by adding a suitable amount of solvent such as petroleum benzine, hexane or petroleum ether to the reaction mixture and then cooling. The residual acid (containing the acid anhydride) in the mother liquor can efficiently be converted to the trans-dichloro-acid by recycling to the heat-isomerization system.

Embodiments of the present isomerization will be illustrated in more details as follows.

Dichloro-acid anhydride

The anhydride is added in an amount of 5 to 30% (by weight) based on the dichloro-acid, or the reagent such as acetic anhydride or thionyl chloride may be added in an amount theoretically required for the formation of the anhydride in the same proportion as above (about 0.02 to 0.2 molar equivalent based on the dichloro-acid).

Lewis acid (p-toluenensulfonic acid, sulfuric acid or the like)

The amount is 2 to 10% (by weight) based on the dichloro-acidd anhydride.

Reaction temperature

The temperature is from 130° to 180° C and preferably from 150° to 170° C.

Reaction period of time

The reaction period of time is from 2 to 15 10 hours.

The present invention will be illustrated with reference to the following examples, which are not to be interpreted as limiting the scope of the present invention.

EXAMPLE 1

A mixture of 8 g of dichloro-acid (cis : trans = 45 : 55), 1.6 g of dichloro-acid anhydride and 0.1 g of p-toluenesulfonic acid was heated at 160° to 165° C for 3 hours and then the cis : trans ratio was measured by gas-chromatography.

Cis : Trans = 21.1 : 78.9

EXAMPLE 2

A mixture of 8 g of dichloro-acid (cis : trans = 45 : 55), 1.2 g of acetic anhydride and 0.1 g of p-toluenesulfonic acid was heated at 160° to 165° C for 3.5 hours while stirring, and then the cis to trans ratio was measured in the same manner as in Example 1.

Cis : Trans = 18.8 : 81.2

EXAMPLE 3

A mixture of 8 g of dichloro-acid (cis : trans = 45 : 55) and 1.2 g of acetic anhydride containing 1% of sulfuric acid was heated at 160° to 165° C. for 3.5 hours, and then the cis to trans ratio was measured in the same manner as in Example 1.

Cis : Trans = 22.5 : 77.5

EXAMPLE 4

A mixture of 8 g of dichloro-acid (cis : trans = 45 : 55), 1.2 g of thionyl chloride and 0.1 g of p-toluenesulfonic acid was heated gradually to 160° to 165° C, and then kept at the same temperature for 3 hours. The cis to trans ratio was then measured in the same manner as in Example 1.

Cis : Trans = 20.6 : 79.4

What we claim is:
1. A process for isomerizing 2-($\beta,\beta$-dichlorovinyl)-3,3-dimethylcylopropanecarboxylic acid represented by the formula

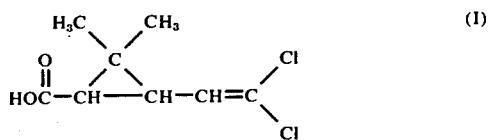

from the cis to the trans form, which comprises heating the acid of the formula (I) in the presence of anhydride of the acid or a reagent producing the acid anhydride in the reaction system selected from the group consisting of acetic anhydride and thionyl chloride, wherein the reaction is carried out in the presence of a catalytic amount of a Lewis acid selected from the group consisting of paratoluenesulfonic acid and sulfuric acid.

2. A process according to claim 10, wherein the amount of the Lewis acid is 2 to 10% by weight based on the weight of the anhydride of the acid of the formula (I).

3. A process according to claim 1, wherein the amount of the acid anhydride is 5 to 30% by weight based on the acid of the formula (I).

4. A process acccording to claim 1, wherein the amount of the reagent producing the acid anhydride in the reaction system is about 0.02 to 0.2 molar equivalent based on the acid of the formula (I).

5. A process according to claim 1, wherein the reaction is carried out at a temperature ranging from 130° to 180° C. for 2 to 15 hours.

6. A process according to claim 5, wherein the reaction is carried out at a temperature ranging from 150° to 170° C.

* * * * *